United States Patent [19]

Takahashi

[11] 4,398,423
[45] Aug. 16, 1983

[54] ULTRASONIC SIGNAL PROCESSING APPARATUS

[75] Inventor: Fuminobu Takahashi, Hitachi, Japan
[73] Assignee: Hitachi, Ltd., Tokyo, Japan
[21] Appl. No.: 224,117
[22] Filed: Jan. 12, 1981
[30] Foreign Application Priority Data
  Jan. 11, 1980 [JP] Japan .................................. 55-1306
[51] Int. Cl.³ ........................................... G01N 29/04
[52] U.S. Cl. ..................................... 73/631; 73/901
[58] Field of Search ................ 73/627, 631, 900, 901

[56] References Cited
U.S. PATENT DOCUMENTS 3,872,715  3/1975  Pittaro .............................. 73/901 X
4,102,205  7/1978  Pies et al. .............................. 73/631

Primary Examiner—Charles A. Ruehl
Attorney, Agent, or Firm—Antonelli, Terry & Wands

[57] ABSTRACT

A defect-responsive echo signal received by a transducer for transmitting and receiving an ultrasonic pulse beam is converted into a digital echo signal by an analog-to-digital converter. The amplitude of the digital echo signal is amended with compensation data stored in correspondence with lapsed times after the ultrasonic pulse beam has been transmitted from the transducer, and an amended echo signal is delivered. The amended echo signal is applied to maximum amplitude value-memory means. First decision means compares a stored value m of the memory means and the amended echo signal delivered anew $n_i$, and alters the stored value of the memory means to $n_i$ when $n_i > m$ holds. Second decision means compares a value m' obtained by attenuating the value m and the value $n_i$, and delivers the stored value m of the memory means as the peak value of the defect-responsive echo when $n_i < m'$ holds and besides $n_i < m$ holds.

5 Claims, 15 Drawing Figures

FIG. 11
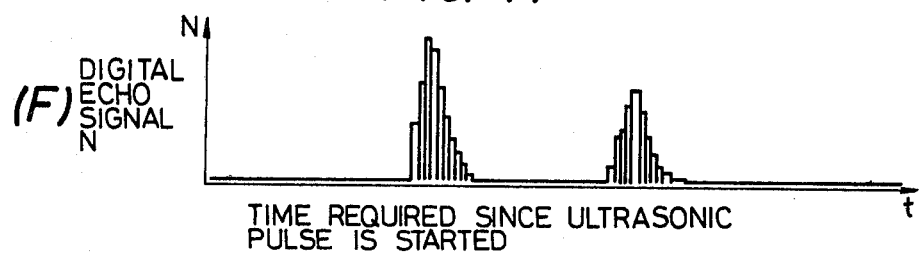
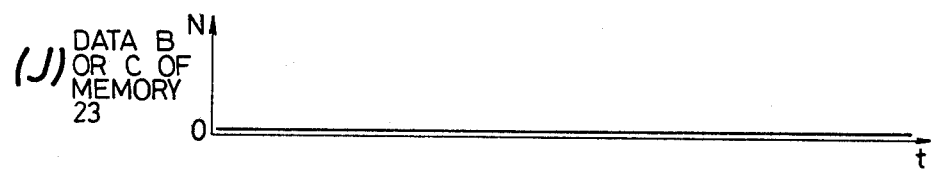
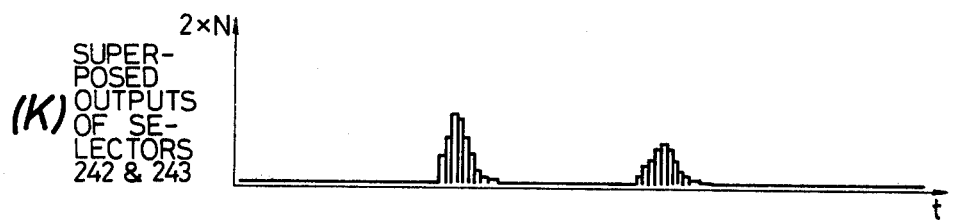
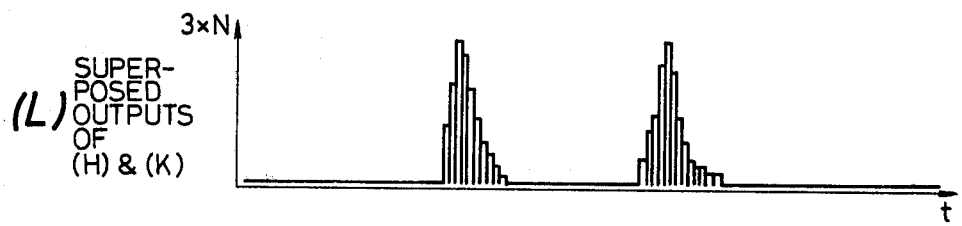
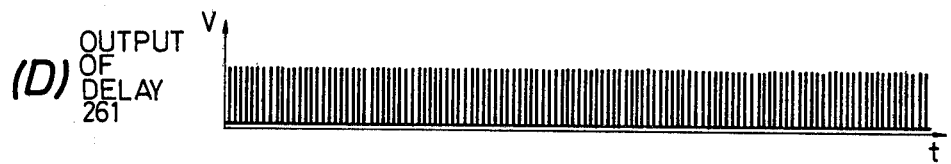
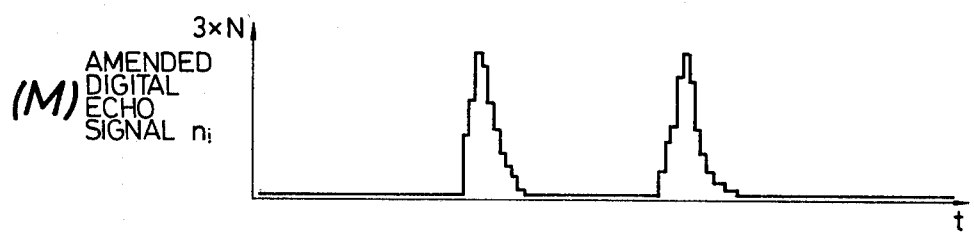

ULTRASONIC SIGNAL PROCESSING APPARATUS

BACKGROUND OF THE INVENTION

This invention relates to an ultrasonic signal processing apparatus for use in ultrasonic flaw detection wherein an ultrasonic pulse is transmitted from an ultrasonic transducer and an echo from a defect in a workpiece is received so as to detect the defect, the apparatus operating to convert into a digital signal the echo signal reflected from the defect in the workpiece.

A prior-art ultrasonic signal processing apparatus which converts into a digital signal an echo signal reflected from a defect in a workpiece and delivers the digital signal as an output is disclosed in, for example, U.S. Pat. No. 3,872,715 entitled "ULTRASONIC PULSE-ECHO GATE CIRCUIT."

SUMMARY OF THE INVENTION

An object of this invention is to provide an ultrasonic signal processing apparatus which, using a digital processing method, can compensate for the inconvenience that the amplitude of an echo signal reflected from a defect in a workpiece attenuates according to the propagation distance of the echo signal, in other words, according to the lapsed time after the transmission of an ultrasonic pulse.

This invention involves the modifying of an echo signal subjected to an analog-to-digital conversion with compensation data stored in advance in correspondence with various lapsed times after the transmission of an ultrasonic signal, thereby making it possible to compensate for the attenuation of an echo signal amplitude attributed to the increase of the propagation distance of the echo signal.

Other objects, features and advantages of this invention will be apparent from the following description taken in conjunction with the accompanying drawings.

BRIEF DESCRIPTION OF THE DRAWINGS

FIGS. 9 to 11 are time charts of signals in various parts of the apparatus shown in FIG. 8.

DESCRIPTION OF THE PREFERRED EMBODIMENTS

Figure 1:
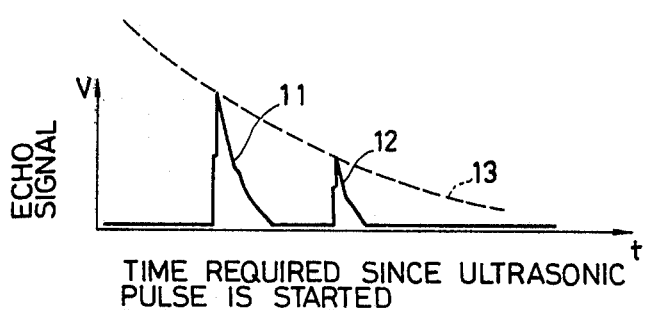
FIG. 1 is a diagram showing the fact that the amplitude of an echo signal from a defect attenuates more as the propagation distance thereof becomes longer.

The axis of abscissa in FIG. 1 represents the time which has lapsed after the generation of an ultrasonic signal, while the axis of ordinates represents the amplitude of a defect-responsive echo signal which is received by an ultrasonic transducer. FIG. 1 illustrates an example in which the propagation distance of a second defect-responsive echo signal 12 is double that of a first defect-responsive echo signal 11. A curve indicated by a broken line 13 depicts the locus of the peak values of the defect-responsive echo signals in the case of detecting an identical defect by means of the identical ultrasonic transducer, the peaks corresponding to the chages of the propagation distance from the defect to the transducer. This curve 13 shall be hereinbelow called the "distance—amplitude amendment curve".

The apparatus of this invention operates so that, as regards an identical defect, defect-responsive echo signals having a fixed peak value are always provided in spite of the changes of the propagation distances of defect-responsive echoes.

Figure 2:
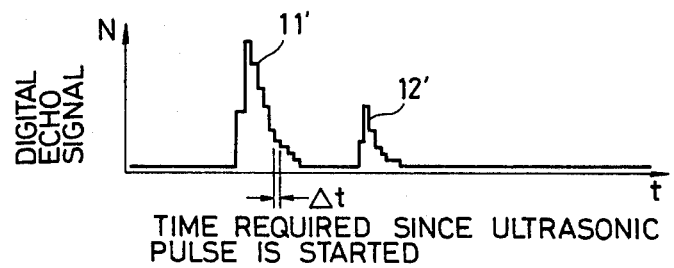
FIG. 2 shows defect-responsive echo signals obtained in such a way that the defect-responsive echo signals shown in FIG. 1 are subjected to an analog-to-digital conversion at intervals of ΔT.
Figure 3:
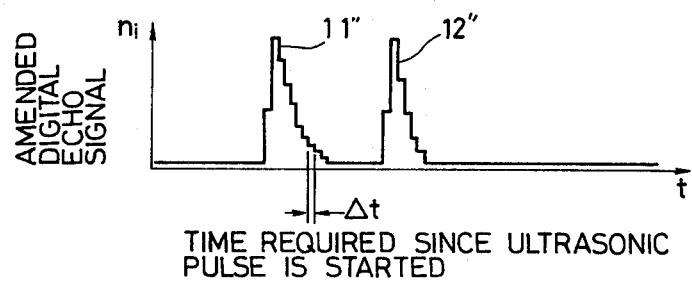
FIG. 3 is a diagram showing the relationship between the propagation distance of a defect-responsive echo signal and the amplitude of an amended defect-responsive echo signal in a first embodiment of this invention in which, with reference to compensation data stored in correspondence with lapsed times after the transmission of an ultrasonic signal, the digital-converted defect-responsive echo signal is subjected to bit-shifting and addition processings thereby to compensate for the attenuation of the amplitude of the defect-responsive echo signal.

A first method according to this invention in which the amplitude of the defect-responsive echo signal is modified in correspondence with the propagation distance thereof (hereunder, this method shall be simply termed the "distance—amplitude amendment method") corresponds to a circuit arrangement shown in FIG. 8 to be described later. In the first distance—amplitude amendment method according to this invention, first of all, the defect-responsive echo signals 11 and 12 shown in FIG. 1 are converted from analog values into digital values at intervals of the lapsed time after the generation of the ultrasonic signal. The digital echo values corresponding to the signals 11 and 12 respectively are illustrated at 11' and 12' in FIG. 2. In FIG. 2, the axis of abscissa represents the lapsed time after the generation of the ultrasonic signal, and Δt indicates each time interval in the case of converting the analog values into the digital values. In the same figure, the axis of ordinates represents the digital value of the amplitude of the defect-responsive echo signal. Amendment values for amending the digital echo signal 12' in FIG. 2 are stored in a memory. The amendment values which are stored in the memory are, for example, values which correspond to the inverse numbers of amplitude values in the distance—amplitude amendment curve 13 shown in FIG. 1. Herein, in an address i of the memory, the amplitude amendment value of the digital echo signal corresponding to the lapsed time after the generation of the ultrasonic signal, $t = \Delta t \times i$ is stored. After the generation of the ultrasonic signal, the amplitude amendment values of the defect-responsive echo signal corresponding to the lapsed times after the generation of the ultrasonic signal (hereinbelow, these amplitude amendment values shall be simply called the "compensation data") are successively read from the respective addresses of the memory at the time intervals $\Delta t$. As will be described later, the digital echo values are bit-shifted in accordance with the compensation data and the bit-shifted echo values are added, whereby amended digital echo signals 11'' and 12'' are obtained as shown in FIG. 3.

Figure 4:
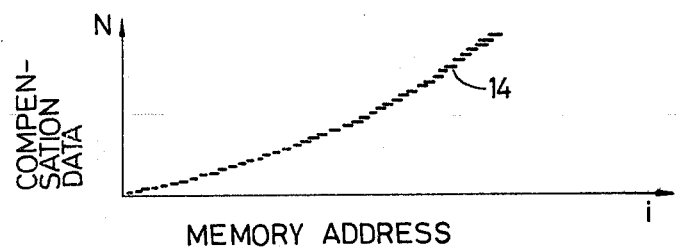
FIG. 4 is a diagram for explaining compensation data of defect-responsive echo signal amplitudes which correspond to lapsed times after the transmission of an ultrasonic signal and which are stored in a memory in order to compensate for the attenuation of the the amplitude of a defect-responsive echo signal as based on the propagation distance thereof in a second embodiment of this invention.
Figure 5:
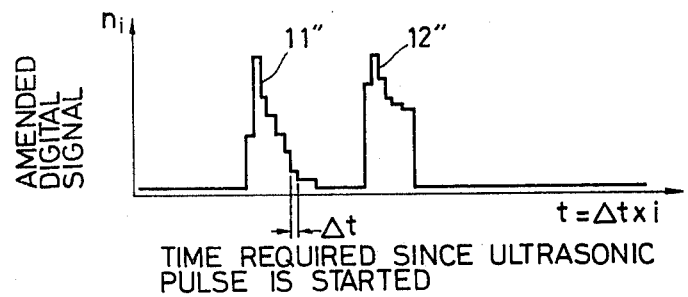
FIG. 5 is a diagram showing the relationship between the propagation distance of a defect-responsive echo signal and the amplitude of an amended defect-responsive echo signal in the second embodiment of this invention in which the compensation data stored in correspondence with the lapsed times after the transmission of the ultrasonic signal as shown in FIG. 4 are added to the digital-converted defect-responsive echo signal.

A second distance—amplitude amendment method according to this invention corresponds to a circuit arrangement shown in FIG. 12 to be described later. In the second distance—amplitude amendement method of this invention, contents to be stored in a memory have a pattern as shown in FIG. 4. The axis of abscissa in FIG. 4 represents the address i of the memory, with which the lapsed time has the proportional relationship of $t = i \times \Delta t$. The axis of ordinates in the same figure represents the value of the compensation data. The pattern 14 in FIG. 4 is identical to a pattern obtained by inverting bilaterally the distance—amplitude amendment curve 13 shown in FIG. 1. Likewise to the first distance—amplitude amendment method of this invention, the second distance-amplitude amendment method of this invention reads the memory contents successively at the time intervals $\Delta t$ and adds the compensation data and the digital echo value. However, whenever the digital echo value is smaller than a fixed value, the added result is made zero. With such method, amended digital echo values as shown in FIG. 5 are obtained.

Figure 6:
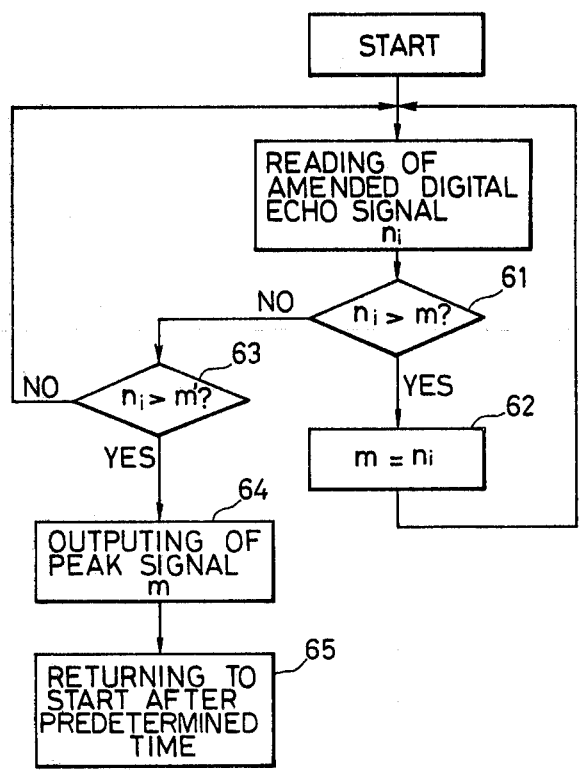
FIG. 6 is a flow chart of a peak detecting mechanism for detecting the amplitude of a defect-responsive echo signal for use in this invention.
Figure 7:
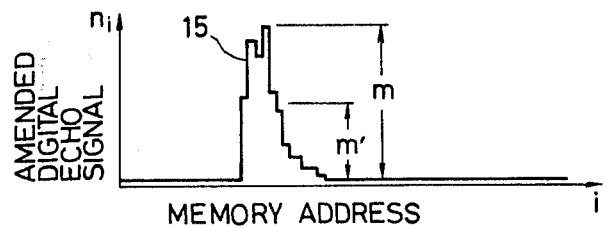
FIG. 7 is a diagram showing an example of the peak detection of digital echo values according to the flow chart showin in FIG. 6.

Now, a peak detecting method according to this invention will be described. The peak detecting method of this invention corresponds to a circuit arrangement shown in FIG. 13 to be described later. The peak detecting method of this invention executes decisions conforming with a flow chart shown in FIG. 6. In a step 60 indicated in FIG. 6, the digital echo value $n_i$ subjected to the distance—amplitude amendment by the first method or second method above described is read. A digital-echo maximum value detected previously, i.e., an initial value m and the echo value $n_i$ are compared in a step 61. If the comparison result is $n_i > m$, a step 62 decides that the digital echo value $n_i$ has approached the peak value and then deems $m = n_i$ so as to return the flow to the step 60 after lapse of a time $\Delta t$. If $n_i \leq m$ holds, there is the possibility that the detected digital echo value has passed the peak value. Therefore, the digital echo value $n_i$ and a value m' (where $0 < m' < m$, $m' = c \cdot m$ and $0 < c < 1$) are compared in a step 63. If $n_i \geq m'$ holds, it is decided that the possibility for the detected digital echo value to have passed the peak value is not very high, and the flow is returned to the step 60 after lapse of the time $\Delta t$. If $n_i < m'$ holds, the step 63 decides that the detected digital echo value has passed the peak value for certainty. On the basis of this decision, the initial value m is provided as an output in a step 64. The output of the initial value m in the step 64 is continued for a predetermined time, and the magnitude of the value m is made $m = 0$ in a step 65 before starting the next peak detection (for example, at the next generation of an ultrasonic signal). According to the flow shown in FIG. 6, as illustrated in FIG. 7, the peak value m can be reliably detected even when the signal-to-noise ratio of a peak part 15 is somewhat inferior. The value m' is selected to be greater than a noise component, and when $n_i < m'$ has held, the peak detection in this invention stops. Accordingly, a malfunction ascribable to a noise component is not involved in the peak detection according to this invention.

Figure 8:
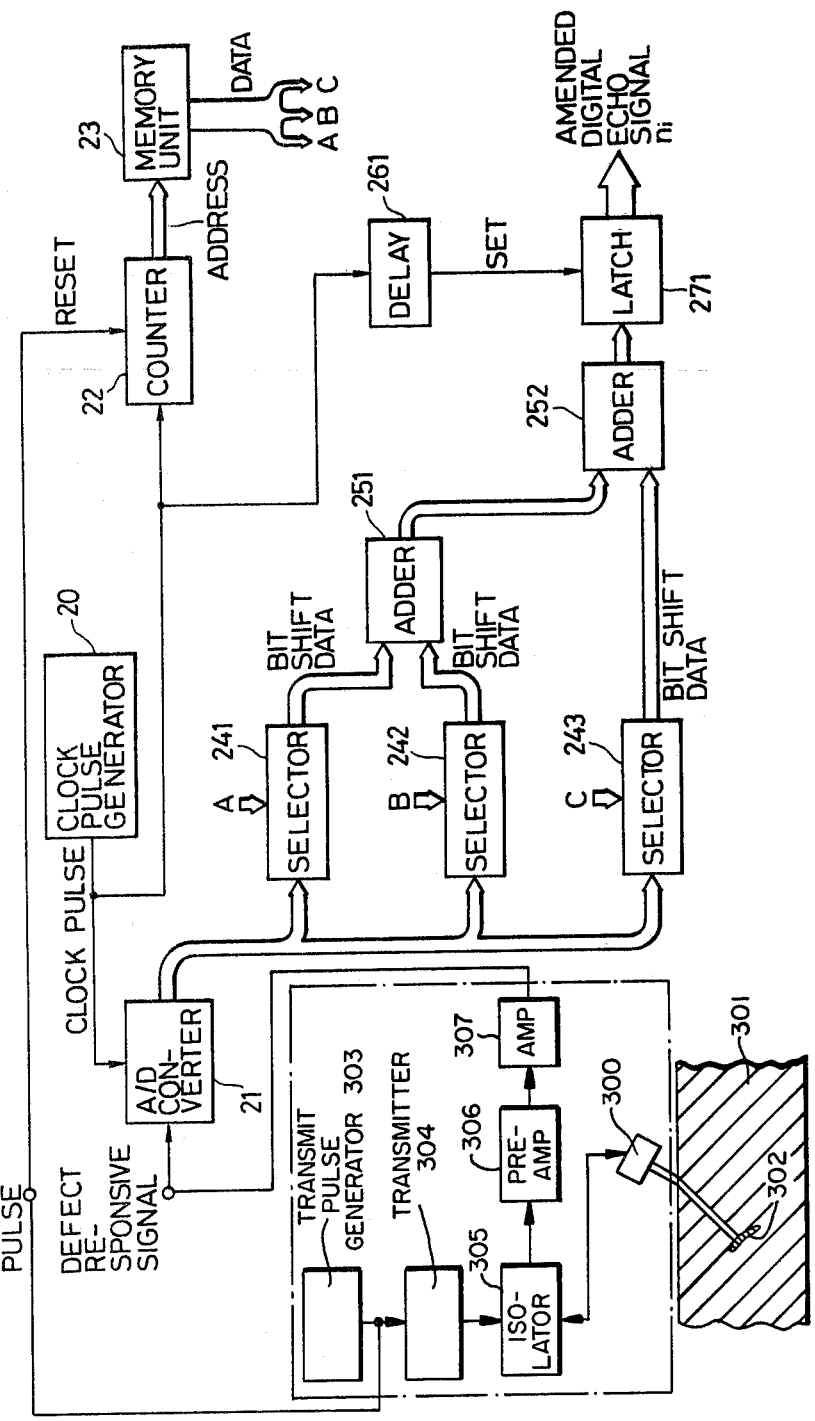
FIG. 8 shows a general block diagram of the first embodiment of this invention except the peak detecting mechanism.

Referring to FIG. 8, the ultrasonic signal processing apparatus of this invention comprises transducer means 308 for transmitting an ultrasonic pulse beam into a workpiece 301 and for receiving an echo signal reflected from a defect 302 in the workpiece 301; an analog-to-digital converter (hereinbelow, abbreviated to "A/D converter") 21 for converting into a digital signal an amplitude value of the echo signal received by the transducer means; a memory unit 23 which stores therein amplitude amendment values of the digital echo signal N to be modified in correspondence with a lapsed time after the ultrasonic pulse beam has been transmitted from the transducer (hereinbelow, simply termed the "lapsed time"); amplitude amendment value-readout means for reading out the amplitude amendment value from the memory unit 23 by supplying the memory unit with a signal corresponding to the lapsed time; and amended amplitude-output means for modifying the amplitude of the digital echo signal N delivered from the A/D converter 21 by the use of the amplitude amendment value read out from the memory unit 23 and for delivering the modified amplitude as an output.

The transducer means 308 consists of a transmit pulse generator 303, a transmitter 304, an isolator 305, a transducer 300, a pre-amp 306 and an amplifier 307. The pulse output from the transmit pulse generator 303 is introduced into the workpiece 301 through the transmitter 304, the isolator 305, and the transducer 300. If the workpiece 301 has a defect 302, the echo signal from the defect 302 is transmitted to the A/D converter 21 through the transducer 300, the isolator 305, the pre-amp 306 and the amplifier 307.

The amplitude amendment value-readout means comprises a counter 22, which is reset by a synchronous pulse from the pulse generator 303, and a clock pulse generator 20 for actuating the counter 22. The counter 22 counts the clock pulses, and causes the memory unit 23 to deliver compensation data stored in its address locations i to selectors 241, 242 and 243 at respective bits of the data. In the embodiment of FIG. 8, the memory contents in each address location of the memory unit 23 consist of the 3 bits A, B and C. Letting $2^n$ be the value of the compensation data (that is, the inverse number of the amendment curve 13 in FIG. 1) corresponding to the address i, the values A, B and C are selected so as to fulfill the relation $2^n = 2^A + 2^B + 2^C$.

The amended amplitude-output means comprises the selectors 241, 242 and 243 for bit-shifting the digital echo signal N from the A/D converter 21 in accordance with the memory contents A, B and C applied to respective data terminals thereof from the memory unit 23 and for performing multiplications between the digital echo signal N and $2^A$, $2^B$ and $2^C$, adders 251 and 252 for adding the bit shift data from the selectors 241, 242 and 243, and a delay 261 as well as a latch 271 for delivering an output of the final-stage adder 252 as an amended digital echo signal $n_i$ after a predetermined time. Here, the adders 251 and 252 are unnecessary for the case where $2^A+2^B+2^C=2^n$, but they are necessary for a case where $2^A+2^B+2^C \neq 2^n$.

Now, the signals of the various parts of the arrangement shown in FIG. 8 will be described with reference to their time charts in FIGS. 9, 10 and 11. In the figure, the axis of abscissa represents the time, the axis of ordinate V represents the voltage, and the axis of ordinate N represents the digital value.

Figure 9:
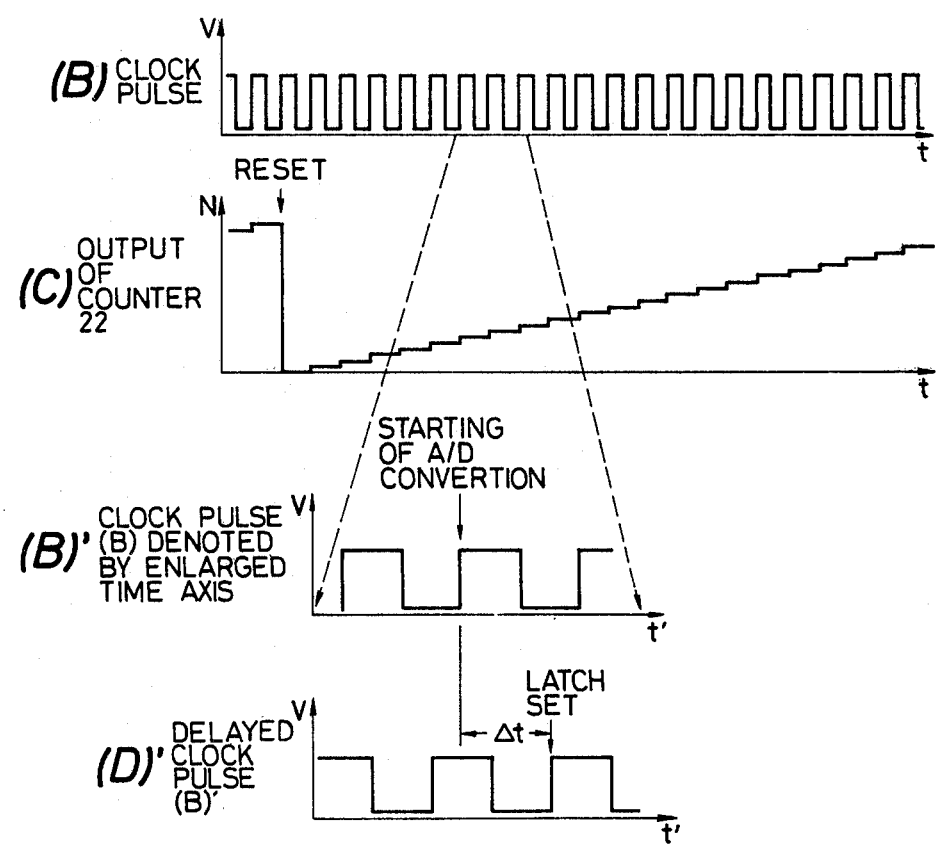

In FIG. 9, a signal shown at (A) is the signal transmission period pulse synchronous with the transmission of the ultrasonic pulse. A signal shown at (B) includes clock pulses provided from the clock pulse generator 20. It is a signal (B)' that denotes the signal (B) on an enlarged time axis. A signal shown at (D)' is obtained by delaying the signal (B)' the time $\Delta t$ by means of the delay 261. A signal shown at (C) indicates the count values of the clock pulses (B) by the counter 22, in other words, values corresponding to the addresses of the memory unit 23, and the count values are reset by the rise of the synchronous pulse shown at (A). The A/D conversion of the A/D converter 21 is started by the rise of the clock pulse shown at (B) and (B)'. The rise of the delayed pulse shown at (D)' becomes the latch timing of the latch 271.

Figure 10:
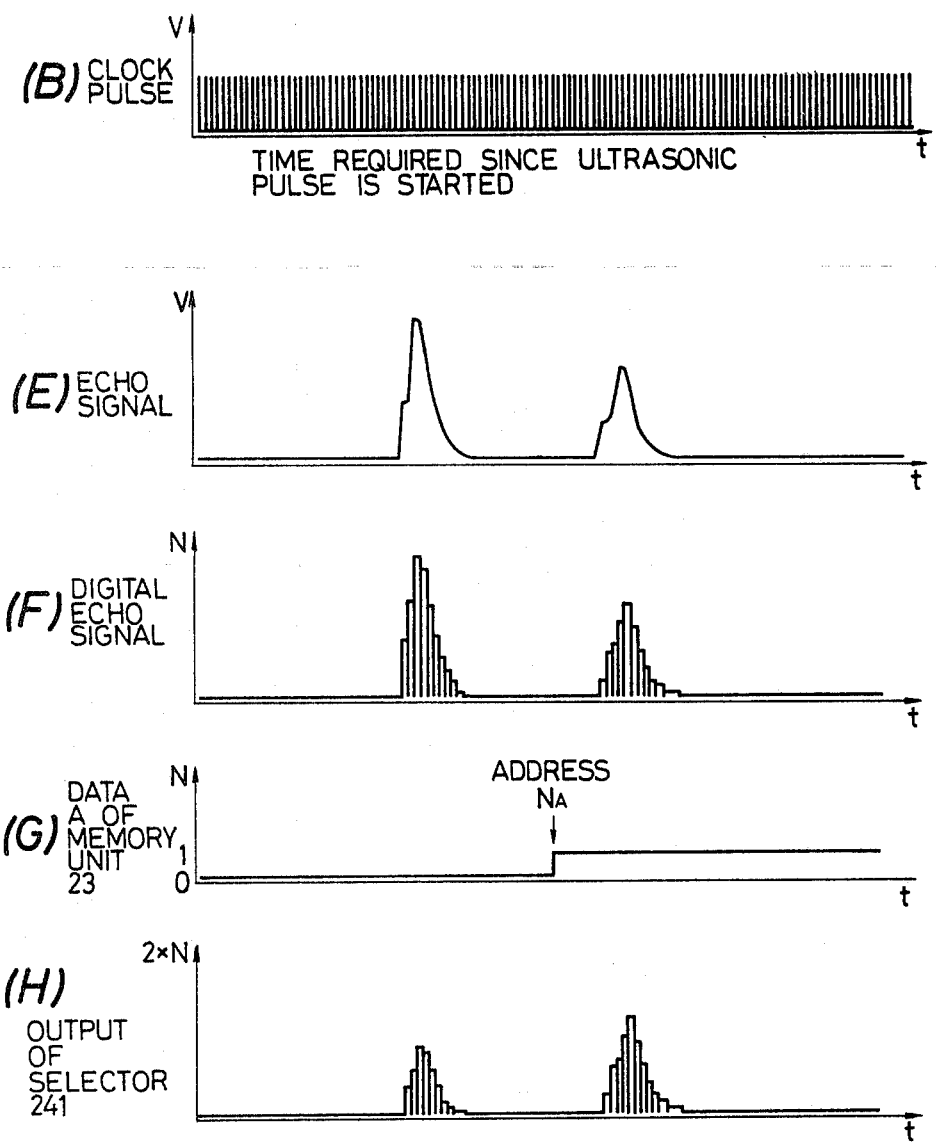

In FIG. 10, a signal shown at (B) corresponds to the clock pulses shown at (B) in FIG. 9 and has the scale of the time axis enlarged. (E) shows two echo signals reflected from an identical defect but having unequal propagation distances. (F) shows digital signals obtained by converting the signals (E) by means of the A/D converter 21. (G) shows an example of the data A of the memory unit 23, in which the data value is 0 (zero) up to an address ($N_A-1$) and is 1 (one) in and beyond an address $N_A$. (H) shows digital values obtained in such a way that the digital echo signals shown at (F) are bit-shifted by the selector 241 in accordance with the data A shown at (G). More specifically, in this example, when the data A is 0 (zero) the signal shown at (F) is delivered as it is, and when the data A is 1 (one) the signal shown at (F) is shifted one bit (is doubled) and the resultant signal is delivered.

In FIG. 11, a signal shown at (F) is the same as depicted at (F) in FIG. 10. (J) shows an example of the value of the data B or data C of the memory unit 23. Here is exemplified a case where both the values of the data B and the data C are 0 (zero). Accordingly, superposed outputs from the selectors 242 and 243 for bit-shifting the digital echo signals shown at (F) in accordance with the data B and the data C become as illustrated in (K). The output waveform at (K) becomes the same as that shown at (F). (L) shows signals obtained in such a way that the signals shown at (H) in FIG. 10 and (K) are added by means of the adders 251 and 252. In this case, the values of the signals at (K) as doubled and the values of the signals at (H) are added. (D) shows the output signal of the delay 261, and corresponds to (D)' in FIG. 9. The latch 271 is actuated by the rise of the delayed clock pulse shown at (D)' so as to latch the output signal of the adder 252 shown at (L), thereby to obtain an amended digital echo signal $n_i$ shown at (M). Since the output of the A/D converter 21 during the A/D conversion operation is unstable as illustrated at (F), the latch processing by the delay 261 is required for obtaining an accurate value after the end of the conversion. Accordingly, the delay time $\Delta t$ of the delay 261 in FIG. 8 is set at a value which is greater than the summation of the maximum conversion time of the A/D converter 21 and the maximum processing times of the selectors 241, 242 and 243 and the adders 251 and 252 and which is smaller than the period of the clock pulses as shown at (D)' in FIG. 9.

Figure 12:
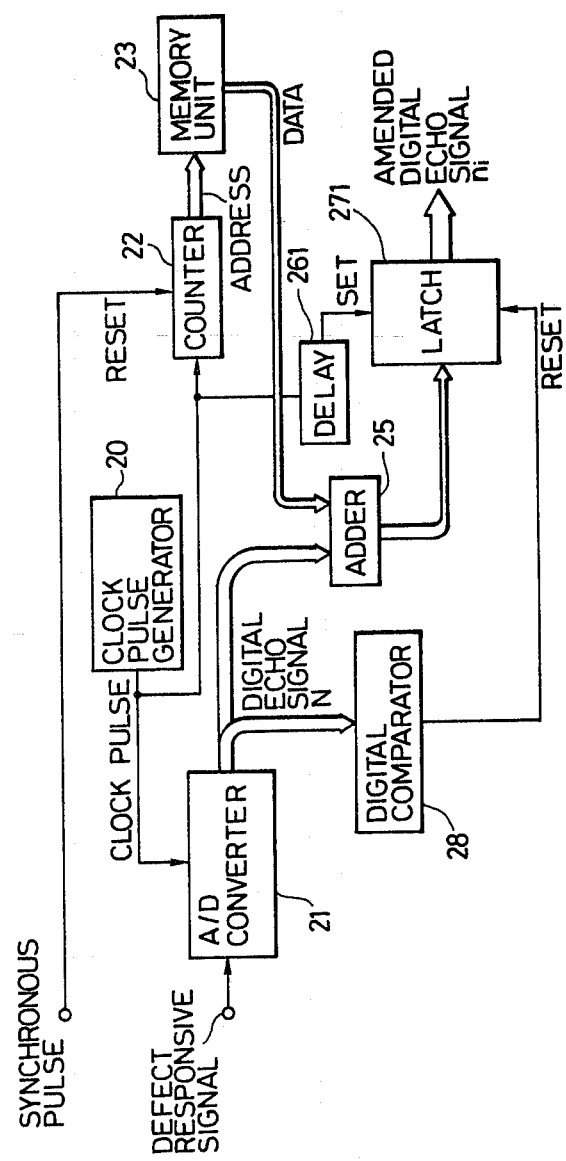
FIG. 12 is a general block diagram of the second embodiment of this invention except the peak detecting mechanism.

FIG. 12 is a block diagram showing the arrangement of a second embodiment of this invention. The difference in construction between the embodiments of FIG. 12 and FIG. 8 is that the former employs a digital comparator 28 without employing the selectors 241, 242 and 243 in the latter. In FIG. 12, an adder 25 adds directly the digital echo signal N from the A/D converter 21 and the compensation data from the memory unit 23 and loads the result into the latch 271. The set timing of the latch 271 is the same as in FIG. 8. However, in the case where the digital echo signal N is smaller than a preset value in the digital comparator 28, this digital comparator delivers a reset signal to the latch 271 to clear the content thereof. The operations of the other portions are quite the same as in FIG. 8.

The time charts of signals in the arrangement shown in FIG. 12 are omitted from the illustration because the same appliances have fundamentally the same timings of signal processings as in the time charts of the signals of the arrangement shown in FIG. 8.

Figure 13:
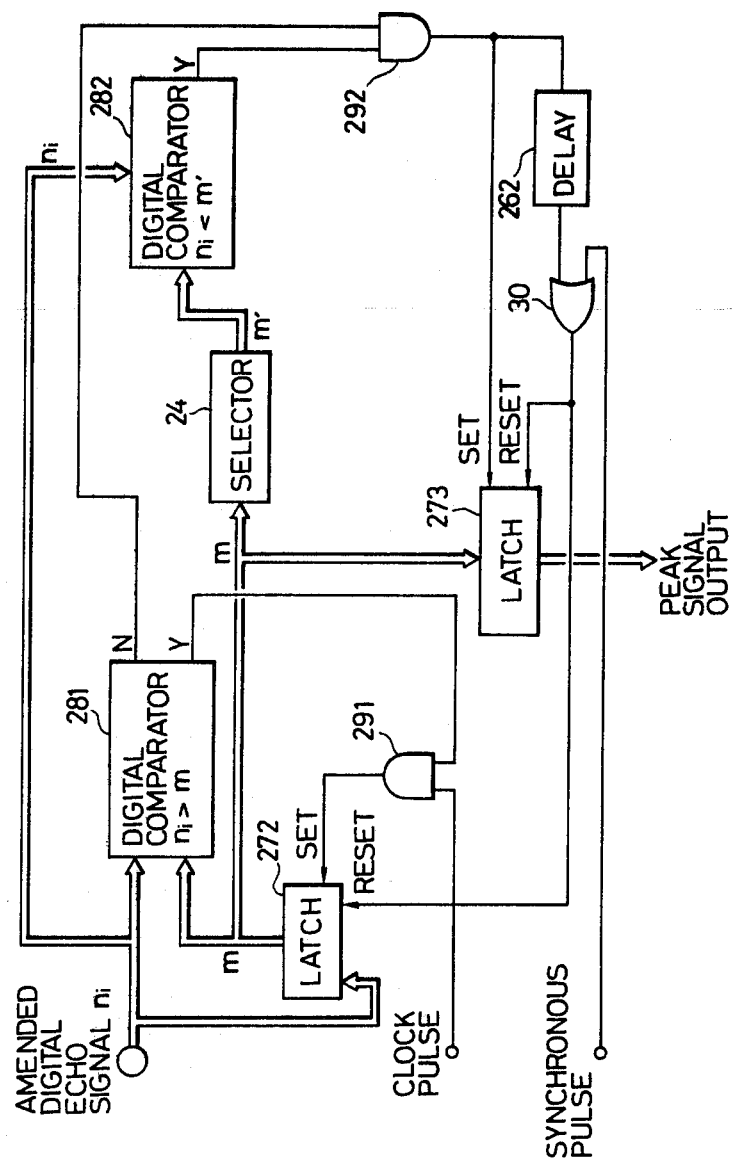
FIG. 13 shows the peak detecting mechanism for use in this invention.

Referring to FIG. 13, a peak detecting mechanism in this invention comprises a latch 272 which is maximum amplitude value-memory means for storing the maximum value m in the amended digital echo signal $n_i$ delivered from the amended amplitude-output means shown in FIG. 8, first decision means for comparing the maximum value m and the amplitude value $n_i$ received anew from the amended amplitude-output means and for latching the stored value of the maximum amplitude value-memory means at the value $n_i$ when $n_i > m$ has held, and second decision means for comparing the value $n_i$ with a value $m'$ obtained by attenuating the value m at a predetermined proportion and for delivering the stored value m of the maximum amplitude value-memory means as a maximum amplitude value on condition that $n_i < m'$ and $n_i < m$ hold.

The first decision means comprises a digital comparator 281 for comparing the amended digital echo signal $n_i$ with the stored value m of the latch 272, and an AND circuit 291 for deeming $m = n_i$ upon receiving a clock pulse and applying this value $n_i$ to the latch 272 when $n_i > m$ has been decided.

The second decision means comprises a selector 24 for bit-shifting the maximum value m stored in the latch 272 serving as the maximum amplitude value-memory means, into the value $m'$ attenuated at the predetermined proportion, a digital comparator 282 for comparing the amended digital echo signal $n_i$ and the attenuated value $m'$ and for delivering an output when $n_i < m'$ holds, an AND circuit 292 for delivering an output signal when the digital comparator 282 has determined that $n_i < m'$ and when at the same time the digital comparator 281 has determined that $n_i < m$, and a latch circuit 273 which is set by the output of the AND circuit 292 to latch the maximum amplitude value m as a peak signal and which is reset by an output of an OR circuit 30 operated by a delayed input from a delay 262 or an input of a synchronous pulse. The operations of the circuit shown in FIG. 13 are as indicated in the flow chart of FIG. 6.

Figure 14:
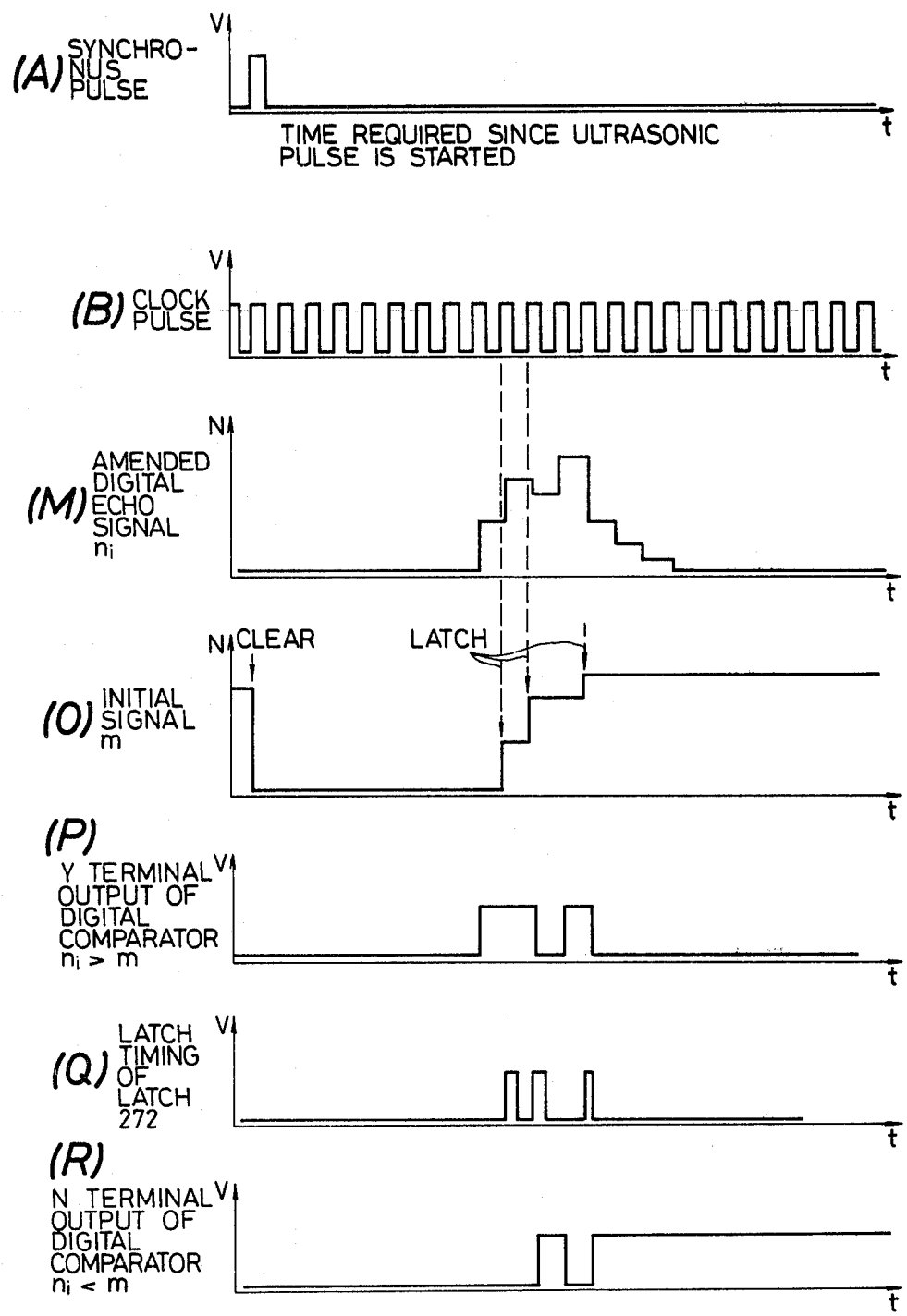
FIGS. 14 and 15 are time charts of signals in various parts of the peak detecting mechanism shown in FIG. 13.
Figure 15:
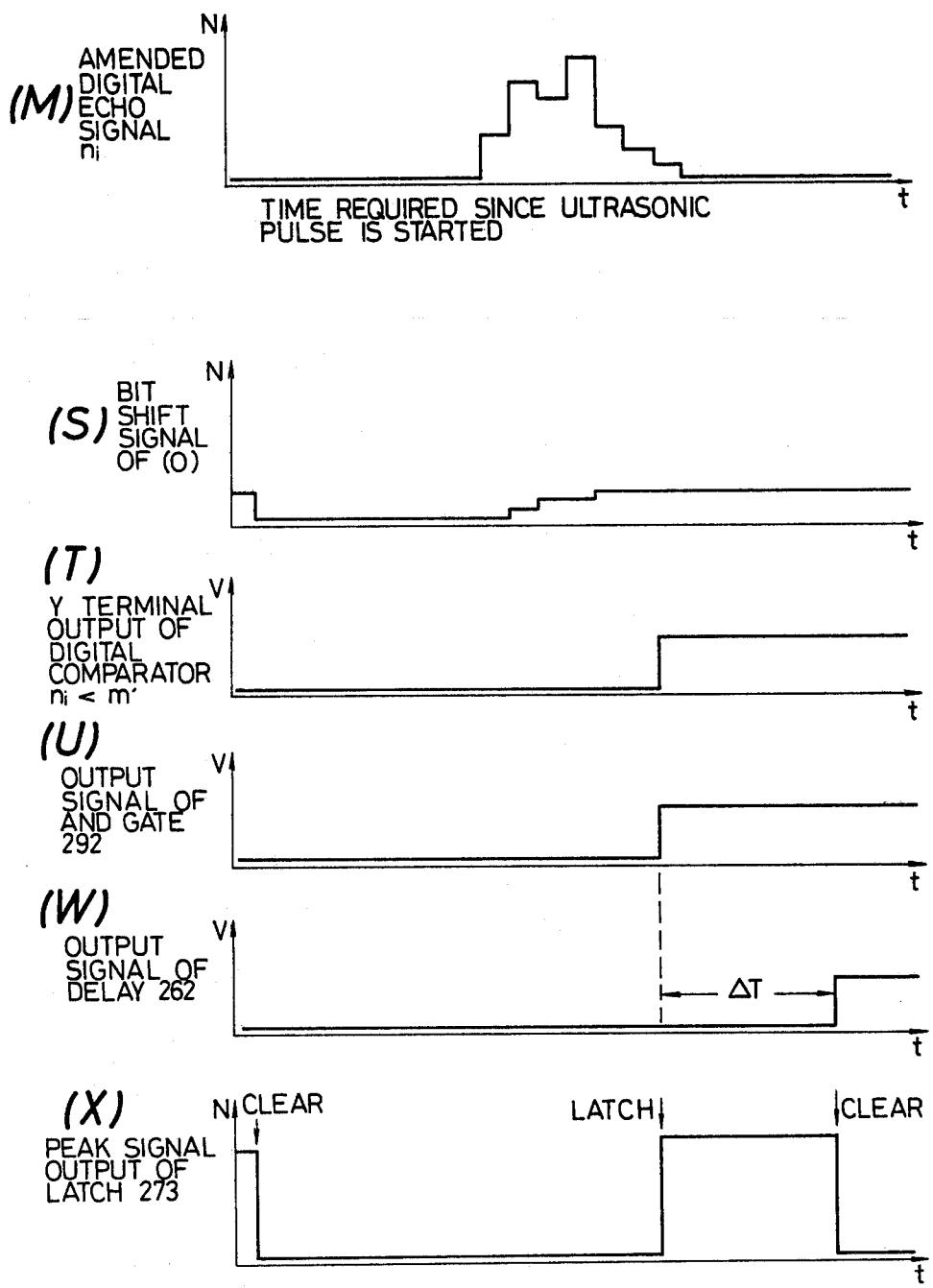

FIGS. 14 and 15 show time charts of the various parts of the arrangement shown in FIG. 13. (A) and (B) in FIG. 14 show the synchronous pulse and the clock pulses in FIGS. 8 and 12, respectively. (M) shows the amended digital echo signal $n_i$ obtained by the arrangement shown in FIG. 8 or 12. (O) represents the maximum amplitude value stored in the latch 272 in FIG. 13, in other words, the initial signal, m, which signal is the output of the latch 272. The initial signal m first becomes 0 (zero) in response to the rise of the synchronous pulse shown at (A), and thereafter becomes $n_i$ in response to the rise of the clock pulse shown at (B) when the amended digital echo signal $n_i$ shown at (M) has become greater than m. (P) indicates the output of the Y terminal of the digital comparator 281, which output becomes level "1" when $n_i > m$ has held. (Q) shows the logical product signal between the clock pulses shown at (B) and the Y-terminal output of the digital comparator 281 shown at (P), and the rise of this logical product signal becomes the latch timing of the latch 272 for providing the initial signal m. (R) shows the N-terminal output signal of the digital comparator 281, and it becomes level "1" when the amended digital echo signal $n_i$ has the relation $n_i < m$.

In FIG. 15, (S) shows the bit shift signal of the initial signal m shown at (O). The signal at (S) or the signal m' is made a value of ¼ (shifted two bits) of the initial signal m shown at (O). Shown at (T) is the Y-terminal output signal of the digital comparator 282 which compares the signal m' shown at (S) with the amended digital echo signal $n_i$ shown at (M). When $n_i < m'$ has held, the level of the Y-terminal output of the digital comparator 282 becomes "1". (U) shows the output signal of the AND circuit 292, which is the logical product signal between the Y-terminal output of the digital comparator 282 illustrated at (T) and the N-terminal output of the digital comparator 281 illustrated at (R) in FIG. 14. The rise of the signal of the digital comparator 282 shown at (T) becomes the latch timing at which the initial signal m shown at (O) in FIG. 14 is set into the latch 273. (W) shows the signal obtained in such a way that the output signal of the AND circuit 292 shown at (U) is delayed ΔT by means of the delay 262. The latch 273 storing the initial signal m shown at (O) in FIG. 14 is cleared by the rise of the signal of the delay 262 shown at (W) and the rise of the synchronous pulse shown at (A) in FIG. 14. (X) in FIG. 15 shows the signal indicative of the peak value from the latch 273. The output signal of the latch 273 shown at (X) becomes 0 (zero) in response to the rise of either the synchronous pulse illustrated at (A) in FIG. 14 or the output signal of the delay 262 illustrated at (W), and becomes the value m in response to the rise of the signal of the AND circuit 292 illustrated at (U). The value m at this time becomes the maximum value of the amended digital echo signal $n_i$. The period of time during which the peak value is delivered is either the shorter one of the period of time from the rise of the signal of the AND circuit 292 shown at (U) to the rise of the next synchronous pulse or the delay time ΔT of the delay 262.

According to this invention, the following effects can be achieved: 1. Since this invention executes the distance-amplitude amendment processings relying on only digital circuitry, it can enhance the amendment precision as compared with the prior art adopting digital circuitry partially.

According to this invention, distance-amplitude compensation errors can be suppressed to below 2%, whereas with the prior art, they become 5% or so. 2. According to the peak detection of this invention, the peak value can be reliably detected even when the signal-to-noise ratio of an echo signal is inferior, and moreover, troublesome settings such as adjustments of the time constants of circuits are dispensed with.

What is claimed is:

1. An ultrasonic signal processing apparatus comprising:

transducer means for transmitting an ultrasonic pulse beam into a workpiece and for receiving an echo signal reflected from a defect in said workpiece;

an analog-to-digital converter for converting into a digital signal an amplitude value of said echo signal received by said transducer means;

a memory unit which stores therein amplitude compensation procedure data for said echo signal to be amended in correspondence with lapsed times after said ultrasonic pulse beam has been transmitted from said transducer means;

amplitude compensation procedure data-readout means for reading out the amplitude compensation procedure data from said memory unit by supplying said memory unit with a signal corresponding to the lapsed time; and amended amplitude-output means for amending the amplitude of said echo signal from said analog-to-digital converter by multiplying said digital signal by a value designated by the compensation procedure data read out from said memory unit.

2. An ultrasonic signal processing apparatus according to claim 1, wherein said amended amplitude-output means includes means for bit-shifting the amplitude value from said analog-to-digital converter in accordance with said amplitude compensation procedure data read out from said memory unit and for delivering the bit-shifted amplitude data as said amended echo signal.

3. An ultrasonic signal processing apparatus according to claim 1, wherein said amended amplitude-output means comprises:

bit-shift means for bit-shifting the amplitude value from said analog-to-digital converter in accordance with a plurality of amplitude compensation procedure data values read out from said memory unit and for delivering the variously bit-shifted amplitude data as respective outputs, and adder means for adding the respective outputs from said bit-shift means and for applying the added result as an output of said amended amplitude-output means.

4. An ultrasonic signal processing apparatus comprising:

transducer means for transmitting an ultrasonic pulse beam into a workpiece and for receiving an echo signal reflected from a defect in said workpiece;

an analog-to-digital converter for converting into a digital signal an amplitude value of said echo signal received by said transducer means;

a memory unit which stores therein amplitude cmpensation data of said echo signal to be amended in correspondence with lapsed times after said ultrasonic pulse beam has been transmitted from said transducer means;

amplitude compensation data-readout means for reading out the amplitude compensation data from said memory unit by supplying said memory unit with a signal corresponding to the lapsed time; and amended amplitude-output means for amending the amplitude of said echo signal by modifying the digital signal from said analog-to-digital converter including amending means for effecting addition or subtraction of said amplitude compensation data read out from said memory unit and the amplitude value delivered from said analog-to-digital converter, latch means for storing the output of said amending means, and comparator means for comparing said digital value to a preset value and for resetting said latch means when said preset value is greater than said digital value.

5. An ultrasonic signal processing apparatus comprising:

transducer means for transmitting an ultrasonic pulse beam into a workpiece and for receiving an echo signal reflected from a defect in said workpiece;

an analog-to-digital converter for converting into a digital signal an amplitude value of said echo signal received by said transducer means;

a memory unit which stores therein amplitude compensation data of said echo signal to be amended in correspondence with lapsed times after said ultrasonic pulse beam has been transmitted from said transducer means;

amplitude compensation data-readout means for reading out the amplitude compensation data from said memory unit by supplying said memory unit with a signal corresponding to the lapsed time;

amended amplitude-output means for amending an amplitude of the echo signal from said analog-to-digital converter by the use of said amplitude compensation data read out from said memory unit and for delivering the amended amplitude;

maximum amplitude value-memory means for storing therein a maximum value of the amplitude values delivered from said amended amplitude-output means;

first decision means for comparing the amplitude value applied anew from said output means and the maximum amplitude value previously applied to said maximum amplitude value-memory means, and for latching the stored value of said maximum amplitude value-memory means to the former value of the comparison under condition that the former value is greater than the latter value; and second decision means for comparing the amplitude value applied anew from said output means and a value obtained by attenuating at a predetermined proportion the maximum amplitude value previously applied to said maximum amplitude value-memory means, and for delivering the stored value of said maximum amplitude value-memory means as the maximum amplitude value under conditions that the latter value of the comparison is greater than the former value and that as the comparison result of said first decision means, said amplitude value applied anew from said output means is smaller than said maximum amplitude value previously applied to said maximum amplitude value-memory means.

* * * * *